United States Patent [19]

Shaikh et al.

[11] Patent Number: 5,334,780
[45] Date of Patent: Aug. 2, 1994

[54] OXIDATION OF HYDROCARBONS OVER ORDERED ARRAYS OF HETEROPOLYACIDS AND POLYOXOANIONS ON GRAPHITE

[75] Inventors: Shahid N. Shaikh, Media; Paul E. Ellis, Jr., Downingtown; James E. Lyons, Wallingford, all of Pa.

[73] Assignee: Sun Company, Inc., Philadelphia, Pa.

[21] Appl. No.: 100,534

[22] Filed: Jul. 30, 1993

[51] Int. Cl.$^5$ .................. C07C 27/12; C07C 31/12; C07C 45/33
[52] U.S. Cl. .................. 568/910; 568/399; 568/910.5
[58] Field of Search .................. 568/910, 399, 910.5

[56] References Cited

U.S. PATENT DOCUMENTS

| | | | |
|---|---|---|---|
| 4,803,187 | 2/1989 | Lyons et al. | 502/200 |
| 4,859,798 | 8/1989 | Lyons et al. | 568/399 |
| 4,864,041 | 9/1989 | Hill | 568/910 |
| 4,898,989 | 2/1990 | Ellis et al. | 568/399 |
| 5,091,354 | 2/1992 | Ellis et al. | 502/200 |

OTHER PUBLICATIONS

Ai, "Partial Oxidation of n-Butane with Heteropoly Compound-based Catalysts," *Proc. 8th Intern. Cong. Catalysis*, Berlin, 1984 *Verlag Chemie*, 5,475–486.

Lyons et al., "Active Iron Oxo Centers for the Selective Catalytic Oxidation of Alkanes," *Structure–Activity and Selectivity Relationships in Heterogeneous Catalysis*, 99–116 (1991) Amsterdam.

Watson et al, "Scanning Tunneling Microscopy of Ordered Hetero and Isopolyanion Arrays on Graphite", *Langmuir*, 8, 1145–1148 (1992).

*Primary Examiner*—Joseph E. Evans
*Attorney, Agent, or Firm*—Stephen T. Falk; Q. Todd Dickinson

[57] ABSTRACT

Alkanes are catalytically oxidized using heteropolyacids (HPAs) or polyoxoanions (POAs) deposited on a graphite surface. The HPAs and POAs are framework-substituted with a different metal in place of a metal-oxygen unit.

25 Claims, No Drawings

OXIDATION OF HYDROCARBONS OVER ORDERED ARRAYS OF HETEROPOLYACIDS AND POLYOXOANIONS ON GRAPHITE

The Government of the United States of America has rights in this invention pursuant to Cooperate Agreement No. DE-FC21-90MC26029 awarded by the U.S. Department of Energy.

BACKGROUND OF THE INVENTION

This invention relates to the oxidation of alkanes with heteropolyacids (HPAs) or polyoxoanions (POAs) supported on a graphite surface. The HPAs and POAs are deposited on the graphite in ordered arrays.

BACKGROUND OF THE ART

The use of HPAs and POAs for the catalytic oxidation of alkanes in air and in liquid phase is known. See, for example, Ai, "Partial Oxidation of n-Butane with Heteropoly Compound-based Catalysts", *Proceedings of the 8th International Congress on Catalysis*, Berlin, 1984, Verlag Chemie, 5, 475; Lyons et al., U.S. Pat. No. 4,803,187; Lyons, et al., U.S. Pat. No. 4,859,798; Ellis et al., U.S. Pat. No. 4,898,989; Ellis et al., U.S. Pat. No. 5,091,354; Lyons et al., *Studies in Surface Science and Catalysis*, 67, 99–116 (1991).

HPAs and POAs and their preparation are described in Pope et al., *Heteropoly and Isopoly Oxo-metalates*, Springer-Verlag, New York (1983). In order to clarify terminology used in the art, consider first a specific precursor of the compositions used in the present invention: $H_3PW_{12}O_{40}$. Since the cations in this material are hydrogen, the compound is referred to as a heteropolyacid. If the cations are not hydrogen, but are metals such as an alkali metal, potassium, sodium or lithium, or are ammonium, as in $K_3PW_{12}O_{40}$ or $(NH_4)_3PW_{12}O_{40}$, then it is no longer an acid, and is referred to as a polyoxoanion.

As described in Pope et al., HPAs and POAs are cage-like structures with a primary, generally centrally located atom(s) surrounded by the cage framework which contains a plurality of other metal atoms, the same or different, bonded to oxygen atoms. Since the central metal atom is different from the other atoms, it is described as "hetero". The other metal atoms are transition metals and have oxygen bonding such as:

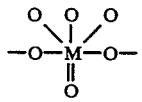

As disclosed in Lyons et al., U.S. Pat. No. 4,859,798, conventional HPAs and POAs may be promoted by the substitution of certain metals in the framework of the HPA or POA with certain other metal atoms. Ellis et al., U.S. Pat. No. 4,898,989, discloses a type of framework substitution wherein three metal atoms in a single triangular face in the HPA/POA framework are replaced with three different metal atoms, thereby enhancing catalytic activity.

A limited set of HPA and POA deposited in ordered arrays on graphite have been characterized. Watson, et al., Scanning Tunneling Microscopy and Tunneling Spectroscopy of Ordered Hetero- and Isopolyanion Arrays on Graphite, *Langmuir*, 8, 1145–1148 (1992), discloses the physical structure of the ordered arrays of HPAs and POAs on graphite as being two-dimensional arrays having periodicities consistent with the molecular dimensions of the molecules.

SUMMARY OF THE INVENTION

The invention involves a method of catalytic oxidation of alkanes using heteropolyacids or polyoxoanions deposited in an ordered array on a graphite surface. The HPAs and POAs are framework-substituted with a different metal in place of metal-oxygen units of the structure.

DETAILED DESCRIPTION OF THE INVENTION

The invention comprises a method of catalytic oxidation of hydrocarbon employing as catalysts heteropolyacids, or polyoxoanions thereof, deposited in an ordered array on a graphite surface. The HPA useful in the invention has the general formula:

$$H_e(X_kM_nM'_zO_y)^{-e}$$

where the central atom X is a Group IIIB-VIB element; M is molybdenum, tungsten or vanadium or combinations thereof; M' is one or more atoms of chromium or other transition metal from Groups IVA, VA, VIIA, VIIIA, IB and IIB of the Periodic Table, substituted in the framework for metal or metal-oxygen unit; k is 1 to 5; z is 1 to 3; n is 5 to 20−z; and y is 18 to 62. The notation "e" is the charge on the $(X_kM_nM'_zO_y)$ group and will vary from case to case; however, "e" is always the number of hydrogen atoms needed to balance the formula. Two preferred classes of HPAs are those in which z is 1-3, n+z is 18, and y is 62−z and those in which z is 1-3, n+z is 12, and y is 40−z. POAs of similar structure deposited on a graphite surface may also be employed in the process of the invention.

In the catalysts useful in the present invention, the central atom X is preferably one, but may be as many as five, atom(s) from Group IIIB, Group IVB, Group VB or Group VIB elements of the Periodic Table. Among these elements, phosphorus, antimony, silicon, boron are preferred; phosphorus being most preferred. The metal M is molybdenum, tungsten or vanadium or combinations thereof. The number of M atoms, n, will vary from 5 to 20−z.

The framework-substituted metal M' is chromium or other transition metal selected from Groups IVA, VA, VIIA, VIIIA, IB and IIB of the Periodic Table. Preferably, M' atoms are selected from Group VIIIA or the first row of Groups IVA–VIIA, i.e., titanium, vanadium, chromium, manganese, iron, cobalt, nickel, ruthenium, rhodium, palladium, osmium, iridium and platinum. Most preferable are the transition metals chromium, manganese, iron, cobalt and ruthenium. The M' atoms must, by definition, be different from the M atoms which they replace. Preferably, the HPA or POA comprises three M' atoms. The three M' atoms do not have to be the same. Except in the case of vanadium, the M' atoms replace M=O units thereby reducing the number of M and O atoms in the HPA or POA by the number of M' atoms, z. When used as M', vanadium remains in a higher oxidation state retaining its terminal oxygen atom.

The conventional and framework-substituted HPAs and POAs may be further promoted with azide; for example, the sodium azide HPA: $H_7(PW_9Fe_2NiO_{37})$-

.NaN$_3$. Other promoters include vanadium, titanium, niobium and rhenium.

The HPAs and POAs may be prepared in the manner known in the art. The procedures therefor described in Lyons et al., U.S. Pat. No. 4,803,187; Ellis et al., U.S. Pat. No. 4,898,989; and Ellis et al., U.S. Pat. No. 5,091,354, are applicable and are hereby incorporated by reference herein. Framework substitution is done prior to deposition of the HPA or POA on the graphite surface.

A method of preparing ordered arrays of the HPAs and POAs on a graphite surface is taught by Watson et al., "Scanning Tunneling Microscopy and Tunneling Spectroscopy of Ordered Hetero- and Isopolyanion Arrays on Graphite", Langmuir, 8, 1145-1148 (1992), and is hereby incorporated by reference herein. In particular, Watson et al. discloses depositing a quantity of an acidic solution (pH=2) of the HPA or POA (0.025M) onto the surface of freshly cleaved highly oriented pyrolyric graphite (HOPG). The solution is then allowed to dry. As disclosed herein, the resulting composition is an effective alkane oxidation catalyst.

Watson et al., supra, discloses that the HPA and POA deposited on HOPG surface form ordered two-dimensional arrays with periodicities corresponding to the molecular dimensions of the molecules. This characteristic is believed to contribute to the effectiveness of the compositions as alkane oxidation catalysts. These catalysts will have good surface coverage of the graphite support surface, a regular array providing a consistent catalyst site and proximate metal centers on the support surface.

The oxidation with ordered arrays of HPA or POA on graphite may be carried out in the presence of a solvent. It should be a relatively unreactive solvent, such as acetonitrile, benzonitrile, benzene, chlorobenzenes and the like. These solvents can yield a single phase homogeneous liquid system for contact with the solid catalyst, although this is not always critical.

In addition to liquid phase operation, the catalysts can be used for vapor phase oxidation of alkanes as well. In this case, the alkane is mixed with an oxygen-containing gas and is contacted with the catalyst, typically in a packed bed reactor. For both liquid and vapor phase operation, the process may be carried out in any conventional reactor configuration.

The oxidation is carried out in liquid phase at 50° to 200° C., preferably 50° to 150° C.; low temperature is an advantage of the invention. The pressure is 0 to 5000 psig, preferably 15 to 1500 psig. Reaction time is 0.1 to 10 hours depending on the conditions and is readily selected by the skilled worker. Vapor phase oxidation is carried out at 150° to 350° C., preferably 150° to 250° C. The pressure is 100 to 1200 psig, preferably 400 to 1000 psig. Gas hourly space velocity is 50 to 50,000 h$^{-1}$, preferably 100 to 10,000 h$^{-1}$. The amount of catalyst employed is generally 0.0001 to 1.0 mmoles catalyst per mole of reactant, preferably 0.0001 to 0.1, but is always a catalytically effective amount.

The alkane starting materials include straight and branched-chain compounds having from about 1 to 20 carbon atoms, preferably 1 to 5, such as methane, ethane, propane, n-butane, isobutane, n-pentane, n-hexane, 2-methylpentane, 3-methylpentane, heptane, 2-methylheptane, 3-methylheptane and the like, as well as cycloalkanes having form about 5 to 20 carbon atoms, preferably 5 to 10 carbon atoms, such as cyclopentane, cyclohexane, cycloheptane, cyclooctane and the like. These compounds, if desired, may be substituted with various moieties, although care should be taken to exclude substituents which will adversely affect the activity of the catalyst.

The process is highly selective for alcohols and ketones, selectivity being defined as a mole percentage of the alkane reacted which is converted to the desired product. In liquid phase, the selectivity to alcohol is usually over 40%, often over 60%, and in some cases over 80%. The selectivity to alcohol and ketone is usually over 90%, frequently over 95%, a truly outstanding result. Small amounts of acids are sometimes formed. The amount of carbon oxides formed is generally under 10%, usually less than .5% and is often under 2%, the percentages being expressed as the mole percent yield of carbon oxides based on the reacted alkane.

EXAMPLE 1

0.10 g of [Fe$_3$W$_9$O$_{37}$]-Na salt on carbon is slurried with O$_2$ (partial pressure=50 psig) and isobutane, 30 ml, at 80° C. and 600 psig total pressure for 3 hours. Oxygen is continuously admitted to maintain a constant partial pressure of 50 psig. The isobutane is steadily converted to a mixture of tert-butyl alcohol, tert-butyl hydroperoxide, ditert-butylperoxide, acetone and minor products. Tert-butyl alcohol is the predominant product.

EXAMPLE 2

A gaseous mixture of ethane and air (3:1; 800 psig) is passed over [Fe$_2$NiW$_9$O$_{37}$]-K salt on graphite, with a GHSV of 500-1000, at 350° C. The ethane is converted to a mixture of ethanol, methanol, formaldehyde, acetaldehyde, carbon monoxide, carbon dioxide, water and minor products. The mixed alcohols, ethanol and methanol, are the major products.

What is claimed is:

1. A method for oxidation of alkanes comprising contacting said hydrocarbon in the presence of oxidant with catalyst comprising (1) heteropolyacid having the formula:

$$H_e(X_kM_nM'_zO_y)^{-e}$$

wherein X is one or more elements selected from a Group IIIB-VIB element; M is molybdenum, tungsten or vanadium or combinations thereof; M' is one or more atoms of chromium or other transition metal from Groups IVA, VA, VIIA, VIIIA, IB and IIB of the Periodic Table, substituted in the framework for one or more metal or metal-oxygen unit k is 1 to 5, z is 1 to 3, n is 5 to 20−z, y is 18 to 62, e is the change on the (X$_k$M$_n$M'$_z$O$_y$) group and the number of hydrogen atoms needed to balance the formula, M' is different from M, and each M' atom is bonded through oxygen to another M or M' atom; or (2) polyoxoanion thereof; wherein said heteropolyacid or polyoxoanion is deposited on a graphite surface.

2. The method of claim 1 wherein said catalyst comprises three M' atoms.

3. The method of claim 1 wherein said atoms of M' are selected from the group consisting of elements from Groups IVA through VIIA, first row, and Group VIIIA of the Periodic Table.

4. The method of claim 3 wherein said atoms of M' are selected from the group consisting of chromium, manganese, iron, cobalt and ruthenium.

5. The method of claim 2 wherein two atoms of M' are selected from the group consisting of chromium, manganese, iron, cobalt and ruthenium, and the third atom is different from said other two atoms.

6. The method of claim 5 wherein said third atom of M' is selected from the group consisting of Group IVA–VIIA, first row, and Group VIII elements.

7. The method of claim 5 wherein two of said M' atoms are iron.

8. The method of claim 1 wherein n+z is 18 and y is 62−z.

9. The method of claim 1 wherein n+z is 12 and y is 40−z.

10. The method of claim 1 wherein X is phosphorus.

11. The method of claim 1 wherein X is silicon.

12. The method of claim 1 wherein M is molybdenum.

13. The method of claim 1 wherein M is vanadium.

14. The method of claim 1 wherein M is tungsten.

15. The method of claim 1 wherein said catalyst is further promoted with azide.

16. The method of claim 1 wherein said polyoxoanion comprises sodium or ammonium salt thereof.

17. The method of claim 1 wherein said oxidation is carried out in liquid phase at a temperature in the range of 50° to 200° C. and a pressure in the range of 0 to 5000 psig for 0.1 to 10 hours.

18. The method of claim 17 wherein said temperature is in the range of 50° to 150° C.

19. The method of claim 17 wherein said pressure is in the range of 15 to 1500 psig.

20. The method of claim 1 wherein said oxidation is carried out in vapor phase at a temperature in the range of 150° to 350° C., a pressure in the range of 100 to 1200 psig, at a gas hourly space velocity of 50 to 50,000 $h^{-1}$.

21. The method of claim 20 wherein said temperature is in the range of 150° to 250° C.

22. The method of claim 20 wherein said pressure is in the range of 400 to 1000 psig.

23. The method of claim 20 wherein said gas hourly space velocity is in the range of 100 to 10,000 $h^{-1}$.

24. The method of claim 1 wherein said oxidant comprises air or oxygen.

25. The method of claim 1 wherein said alkane contains 1 to 20 carbon atoms.

* * * * *